United States Patent
Islam et al.

(10) Patent No.: US 10,096,785 B2
(45) Date of Patent: Oct. 9, 2018

(54) TETRACENOTHIOPHENE DERIVATIVES WITH ALKOXY-C-ALKYNE SOLUBILISING UNITS AND THEIR APPLICATIONS AS ORGANIC SEMICONDUCTORS

(71) Applicants: Cambridge Display Technology Limited, Godmanchester (GB); Sumitomo Chemical Company Limited, Tokyo (JP)

(72) Inventors: Nazrul Islam, Cambridgeshire (GB); Eiji Yoshikawa, Tsukuba (JP)

(73) Assignees: Cambridge Display Technology Limited, Godmanchester (GB); Sumitomo Chemical Company Limited, Tokyo (JP)

(*) Notice: Subject to any disclaimer, the term of this patent is extended or adjusted under 35 U.S.C. 154(b) by 119 days.

(21) Appl. No.: 15/333,831

(22) Filed: Oct. 25, 2016

(65) Prior Publication Data
US 2017/0133605 A1    May 11, 2017

(30) Foreign Application Priority Data
Nov. 6, 2015  (GB) .................................. 1519625.6

(51) Int. Cl.
| | |
|---|---|
| *H01L 51/00* | (2006.01) |
| *C07D 333/50* | (2006.01) |
| *C09D 5/24* | (2006.01) |
| *H01L 51/05* | (2006.01) |
| *H01L 51/50* | (2006.01) |
| *H01L 51/56* | (2006.01) |

(52) U.S. Cl.
CPC ........ *H01L 51/0074* (2013.01); *C07D 333/50* (2013.01); *C09D 5/24* (2013.01); *H01L 51/0002* (2013.01); *H01L 51/0558* (2013.01); *H01L 51/5012* (2013.01); *H01L 51/56* (2013.01)

(58) Field of Classification Search
CPC . H01L 51/00; H01L 51/0074; H01L 51/0002; H01L 51/0558; H01L 51/5012; H01L 51/56; C07D 333/50; C09D 5/24
USPC ........ 252/500; 257/40, E51.024; 549/29, 41; 427/58
See application file for complete search history.

(56) References Cited

U.S. PATENT DOCUMENTS

| | | | |
|---|---|---|---|
| 7,655,809 B2 * | 2/2010 | Fallis ...................... | C07B 37/12 257/40 |
| 2008/0142793 A1 * | 6/2008 | Tang .................... | C07D 333/50 257/40 |
| 2017/0331042 A1 * | 11/2017 | Kim .................... | H01L 51/0035 |

FOREIGN PATENT DOCUMENTS

| | | |
|---|---|---|
| WO | WO 2006/107591 A | 10/2006 |
| WO | WO 2006/119853 A | 11/2006 |

OTHER PUBLICATIONS

Quan Yuan et al., "Thin Film Structure of Tetraceno[2,3-b]thiophene Characterized by Grazing Incidence X-ray Scattering and Near-Edge X-ray Absorption Fine Structure Analysis", J. Am. Chem.Soc.Soc., 2008, 130, 3502-3508. (Year: 2008).*
Combined Search and Examination Report for related Application No. GB1519625.6, dated Aug. 31, 2016, pp. 1-5.

* cited by examiner

*Primary Examiner* — Douglas J McGinty
(74) *Attorney, Agent, or Firm* — Wolf, Greenfield & Sacks, P.C.

(57) ABSTRACT

Tetracenothiophene derivatives are disclosed, which comprise alkoxy-C-alkyne solubilizing groups at transversal positions of the tetracenothiophene unit. These compounds enable preferential molecular stacking and a high field effect mobility and at the same time show improved solubility as compared to known benzothiophene- and pentacene-based materials. In addition, organic thin films comprising these derivatives, their use in electronic devices and components, such as organic thin film transistors, and methods of manufacturing the same are disclosed.

15 Claims, 3 Drawing Sheets

TETRACENOTHIOPHENE DERIVATIVES WITH ALKOXY-C-ALKYNE SOLUBILISING UNITS AND THEIR APPLICATIONS AS ORGANIC SEMICONDUCTORS

RELATED APPLICATIONS

This application claims the benefits under 35 U.S.C. § 119(a)-(d) or 35 U.S.C. § 365(b) of British application number 1519625.6, filed Nov. 6, 2015, the entirety of which is incorporated herein.

FIELD OF INVENTION

This invention relates to novel tetracenothiophene derivatives, organic thin films comprising these derivatives, their use in electronic devices and components, and to methods of manufacturing the same.

BACKGROUND OF THE INVENTION

In the recent years, there has been increased interest in the development of small-molecule organic electronic materials as alternatives to inorganic semiconductors, such as silicon-based semiconductors, as they are lightweight, provide a high flexibility and allow manufacturing and processing of electronic devices at relatively low costs. Typically applied within thin films, such organic semiconductors find use in a large number of electronic devices, such as displays (including organic light-emitting diodes (OLED)), photovoltaics, and electronic circuits and components (e.g. organic field effect transistor (OFET) devices).

Ideally, organic semiconductors exhibit high charge carrier mobility or high field effect mobility, respectively, and favourable π-π stacking. Organic semiconductors fulfilling these criteria tend to be those which comprise compounds having a rigid planar structure and extensively conjugated π-systems allowing for the movement of electrons. In addition, it is of utmost importance that organic semiconductors are both highly soluble and thermally stable during solution processing.

Pentacene derivatives comprising trialkylsilylethynyl groups as solubilising groups, such as e.g. 6,13-bis[(triisopropylsilyl)ethynyl] pentacene (commonly referred to as "TIPS-pentacene"), have been widely used in view of their favourable solubility and stability in organic solvents as well as the performance in organic field effect transistors (see e.g. U.S. Pat. No. 6,690,029 B1).

In the recent years, efforts have been made to synthesize and investigate the charge carrier mobility performance of alternatives to TIPS-pentacene. To this end, the replacement of the pentacene core with other acene-based structures has been studied. Tang et al., Chem. Mater. 2008, 20(14), 4669-4676; Tang et al., J. Am. Chem. Soc. 2009, 131(14), 5264-5273; EP 1880 429 B1; US 2008/0191199 A1; and US 2009/0299070 A1 disclose that 5,12-bis(trialkylsilylethynyl) tetraceno[2,3-b]thiophenes represent promising candidates, particularly in view of their stable charge mobility when used in combination with organic binder materials, which are typically applied in order to improve the uniformity and integrity of organic thin films.

Palayangoda et al., J. Org. Chem. 2007, 72(17), 6584-6587 further disclose 5,12-bis(trialkylsilylethynyl)tetraceno[2,3-b]thiophenes bearing methoxy groups at the 6- and 13-positions of the tetraceno[2,3-b]thiophene core, which exhibit improved photooxidative stability.

However, since the hitherto disclosed compounds still leave room for improvements, it is desirable to provide alternative compounds that exhibit high field effect mobility, favourable π-π stacking, and at the same time show improved solubility and thermal stability during solution processing when compared to existing small-molecule organic semiconductors.

SUMMARY OF THE INVENTION

The present invention solves this object with the subject matter of the claims as defined herein. The advantages of the present invention will be further explained in detail in the section below and further advantages will become apparent to the skilled artisan upon consideration of the invention disclosure.

In the search for soluble, small molecule organic semiconductor materials for thin film transistor device applications, materials that exhibit a crystalline structure enabling a high field effect mobility and an improved solubility as compared to known benzothiophene based materials have been studied. The present inventors surprisingly found that implementation of specific transverse solubilising groups at the 5- and 12-positions of the tetraceno[2,3-b]thiophene core remarkably improves the solubility whilst still maintaining the preferential molecular packing motif in the solid crystal required to achieve high field effect mobilities, thereby providing a solution to the abovementioned problems.

Generally speaking, in one aspect the present invention relates to a tetracenothioacene derivative represented by the following General Formula (I):

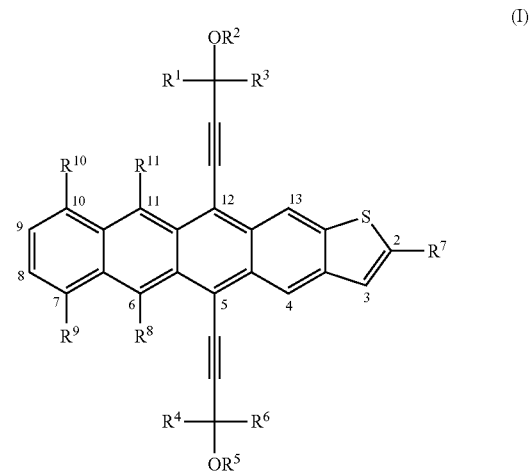

wherein $R^1$ to $R^6$ independently represent a $C_{1-12}$ alkyl group; wherein $R^8$ to $R^{11}$ independently represent any one of a hydrogen atom, a halogen atom, or a $C_{1-6}$ alkyl group; and wherein $R^7$ represents any one of a hydrogen atom, a halogen atom, a $C_{1-12}$ alkyl group or a substituent according to the following General Formula (II):

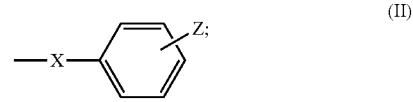

X being a single bond, —S— or —SO$_2$—; and Z being a C$_{1-12}$ alkyl group.

In a further aspect, the present invention provides an organic thin film comprising the above-described tetracenothiophene derivatives.

Another aspect of the present invention is an electronic device or component comprising said an organic thin film.

Preferred embodiments of the tetracenothioacene derivatives according to the present invention and other aspects of the present invention are described in the following description and the claims.

DETAILED DESCRIPTION OF THE INVENTION

Figure 1:
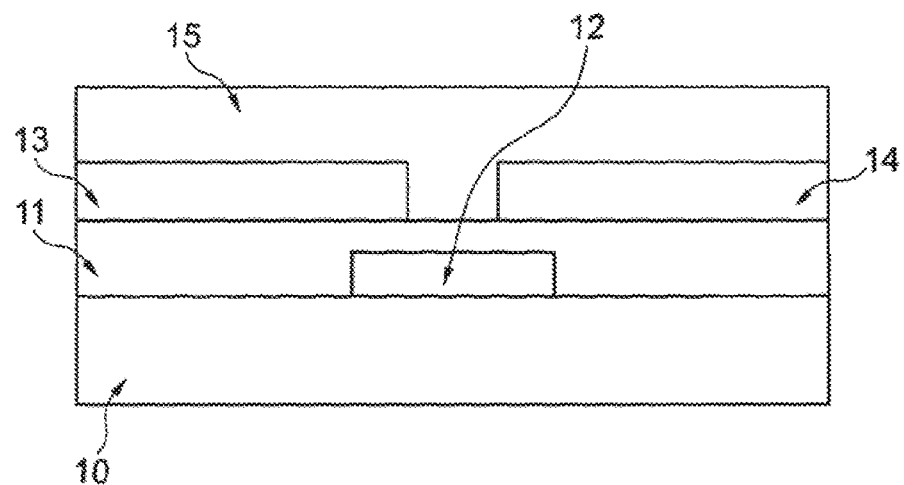
FIG. 1 schematically illustrates the general architecture of a conventional bottom-gate organic thin film transistor.

For a more complete understanding of the present invention, reference is now made to the following description of the illustrative embodiments thereof:
Tetracenothiophene Derivatives In a first embodiment, the present invention relates to tetracenothiophene derivatives, the most general structure of which may be represented by the following General Formula (I):

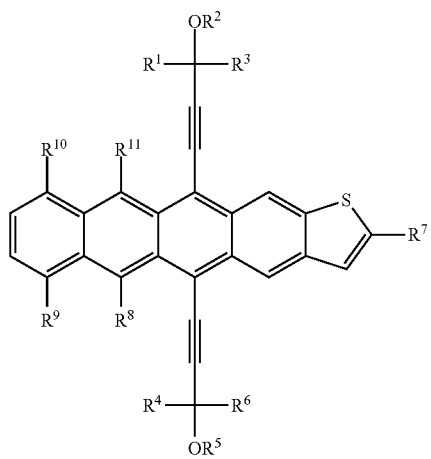

Herein, R$^1$ to R$^6$ independently represent a C$_{1-12}$ alkyl group, preferably a C$_{1-6}$ alkyl group, more preferably an alkyl group selected from any of a methyl, ethyl, isopropyl or tert-butyl group.

Preferably, the substituents R$^1$, R$^3$, R$^4$ and R$^6$ in General Formula (I) are independently selected from any of a methyl, ethyl, isopropyl or tert-butyl group.

If R$^1$ differs from R$^3$ and/or R$^4$ differs from R$^6$, the carbon atoms to which the groups R$^1$, —OR$^2$ and R$^3$; and/or R$^4$, —OR$^5$, R$^6$ are attached form one or two chiral centres, respectively. In this regard, it is to be understood that General Formula (I) according to the present invention encompasses all variants of possible stereoisomers.

In another preferred embodiment, R$^2$ and/or R$^5$ are methyl or ethyl groups, more preferably methyl groups. In a further preferred embodiment, R$^2$ and R$^5$ are identical.

In General Formula (I), R$^8$ to R$^{11}$ independently represent any one of a hydrogen atom, a halogen atom, or a C$_{1-6}$ alkyl group. In further preferred embodiments, R$^8$ and R$^{11}$ represent hydrogen and R$^9$ and R$^{10}$ are independently selected from a halogen atom or a C$_{1-6}$ alkyl group, or R$^9$ and R$^{10}$ represent hydrogen and R$^8$ and R$^{11}$ are independently selected from a halogen atom or a C$_{1-6}$ alkyl group. In another preferred embodiment, R$^8$ and R$^{11}$ and/or R$^9$ and R$^{10}$ are identical. With regard to substituents R$^8$ to R$^{11}$, a fluorine atom is preferably used as the halogen atom and as C$_{1-6}$ alkyl group, a methyl group is further preferred.

In General Formula (I), R$^7$ represents any one of a hydrogen atom, a halogen atom, a C$_{1-12}$ alkyl group or a substituent according to the following General Formula (II):

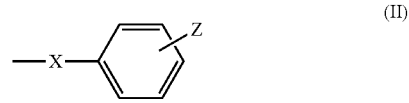

wherein X is a single bond, —S— or —SO$_2$—, preferably S— or —SO$_2$—; and Z represents a C$_{1-12}$ alkyl group preferably a C$_{1-6}$ alkyl group, more preferably an alkyl group selected from any of a methyl, ethyl, isopropyl or tert-butyl group. While not being limited thereto, the halogen atom is preferably a fluorine atom. If R$^7$ is represented by a C$_{1-12}$ alkyl group, the alkyl group is preferably a C$_{1-6}$ alkyl group, more preferably an alkyl group selected from any of a methyl, ethyl, isopropyl or tert-butyl group.

In a preferred embodiment, the substituent Z is in para-position relative to the substituent X in accordance with the following General Formula (III), or bond in para-position relative to the thienyl group if X is a single bond:

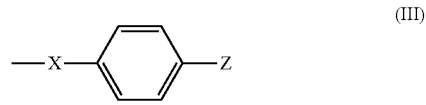

In a preferred embodiment of General Formula (I), R$^1$ and R$^3$ are identical and/or R$^4$ and R$^6$ are identical. More preferably, R$^1$, R$^3$, R$^4$ and R$^6$ are identical.

In another preferred embodiment, the residues R$^1$, R$^3$, R$^4$ and R$^6$ differ from the substituent Z.

In an alternatively preferred embodiment the residues R$^1$, R$^3$, R$^4$, R$^6$ and the substituent Z are identical.

It will be appreciated that the preferred features specified above may be combined in any combination, except for combinations where at least some of the features are mutually exclusive.

The above compounds have been shown to exhibit a particularly favourable balance in terms of high field effect mobility, favourable π-π stacking, and thermal stability during solution processing. Last but not least, these compounds are easily soluble and may thus be applied by a large variety of solution deposition techniques.
A number of exemplary compounds illustrating the present invention are listed hereinbelow:
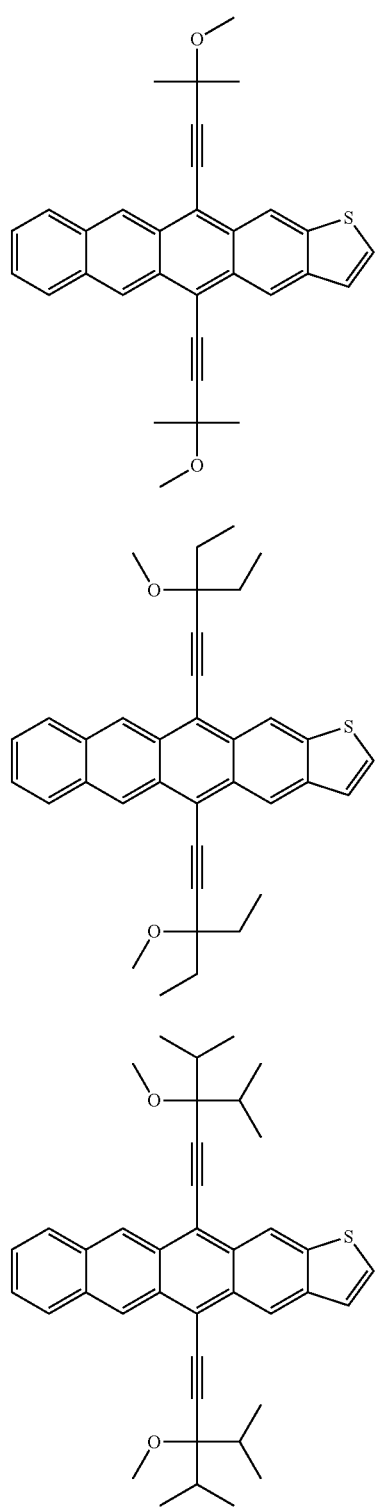
(1)
(2)
(3)
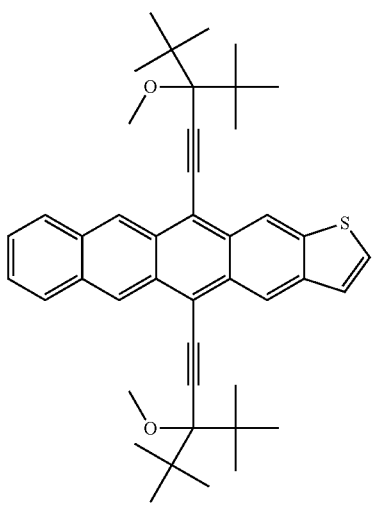
(4)
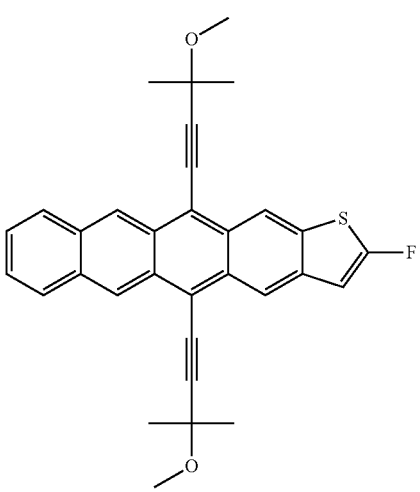
(5)
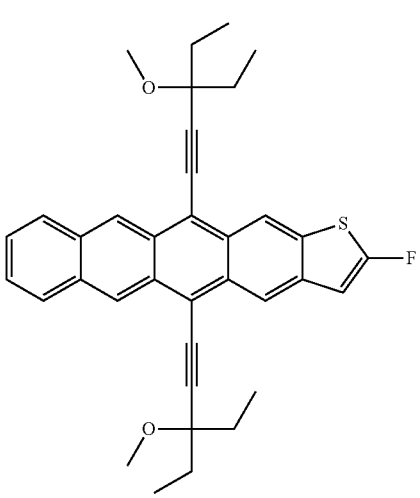
(6)

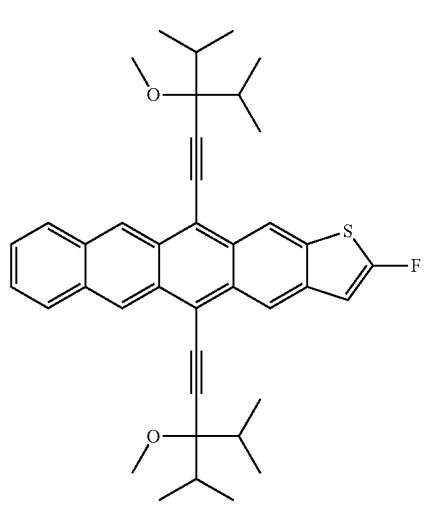
(7)
(8)
(9)
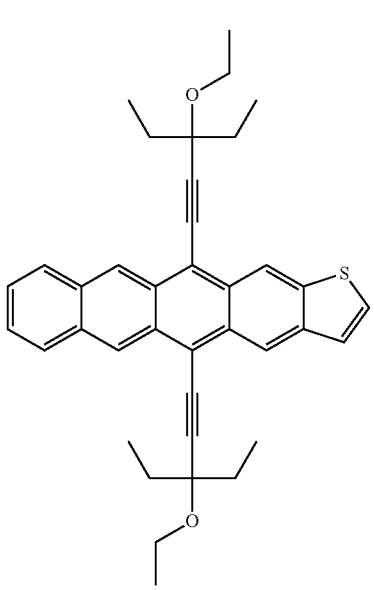
(10)
(11)
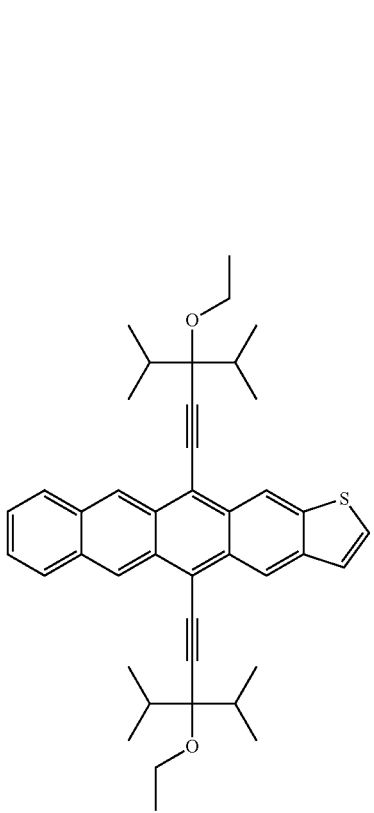

(12)
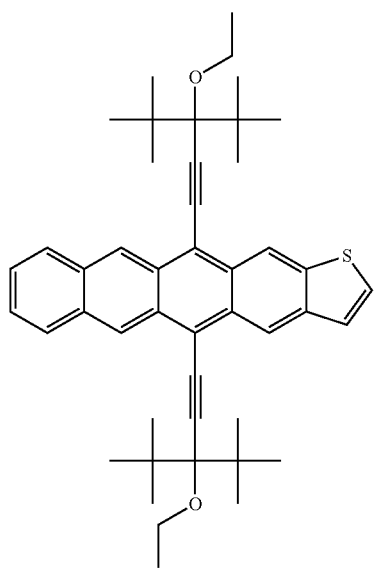
(15)
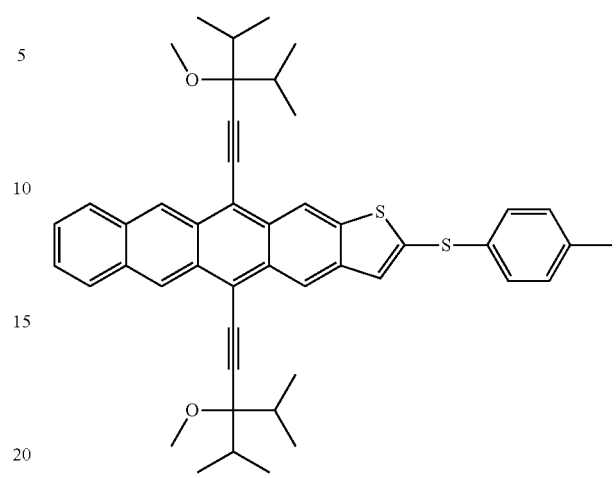
(13)
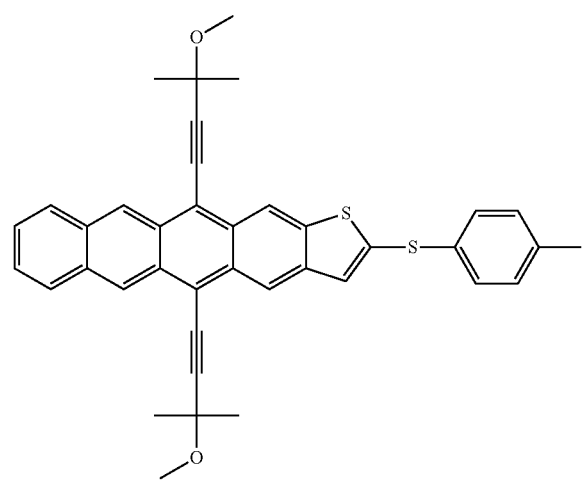
(16)
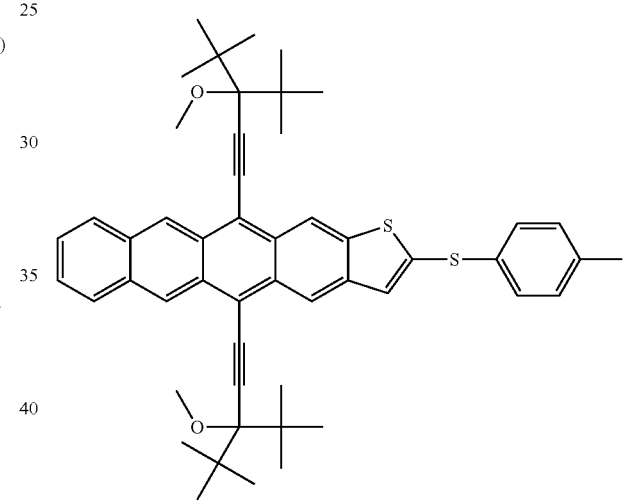
(14)
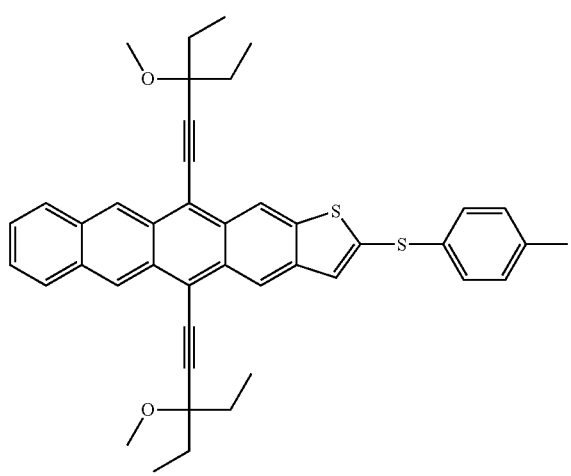
(17)
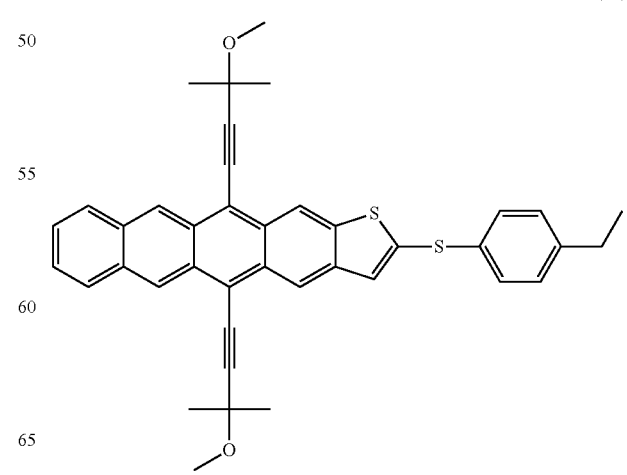

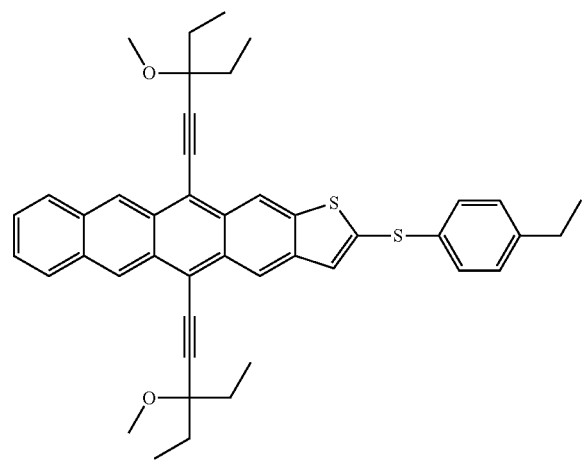
(18)
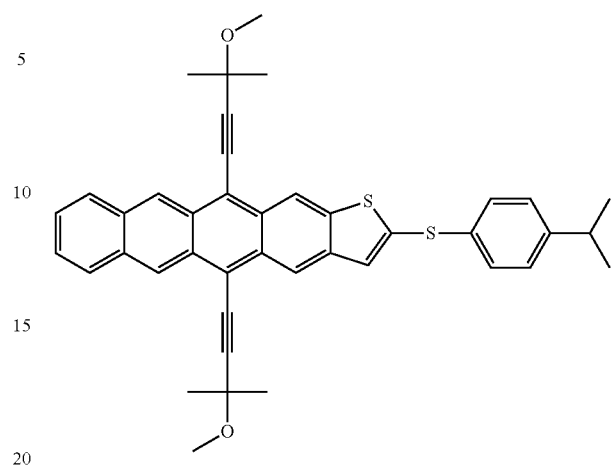
(21)
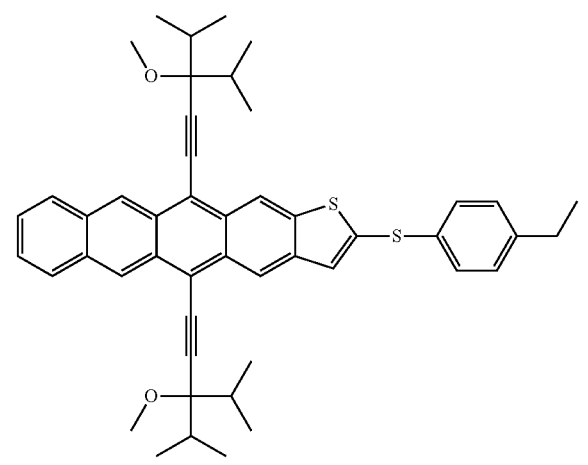
(19)
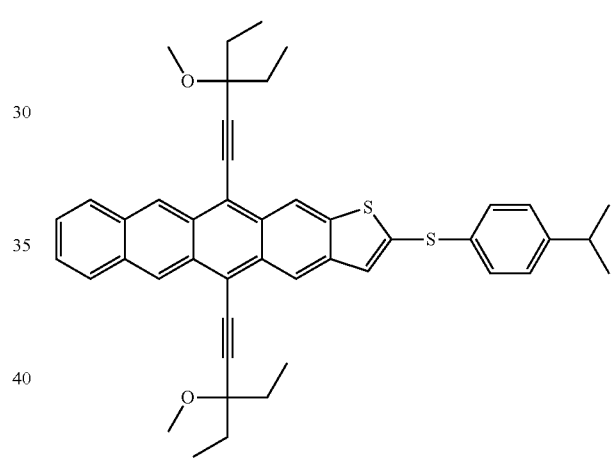
(22)
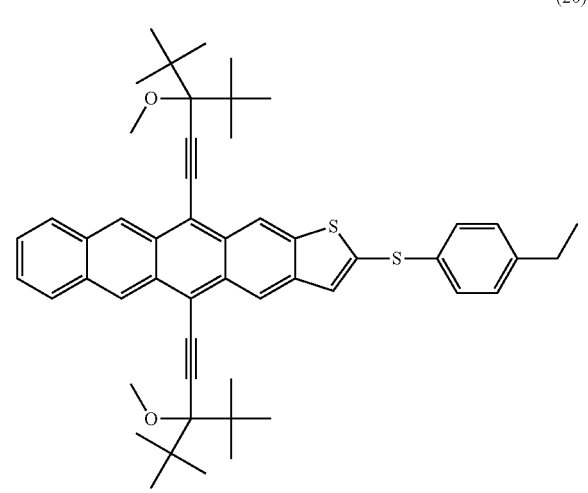
(20)
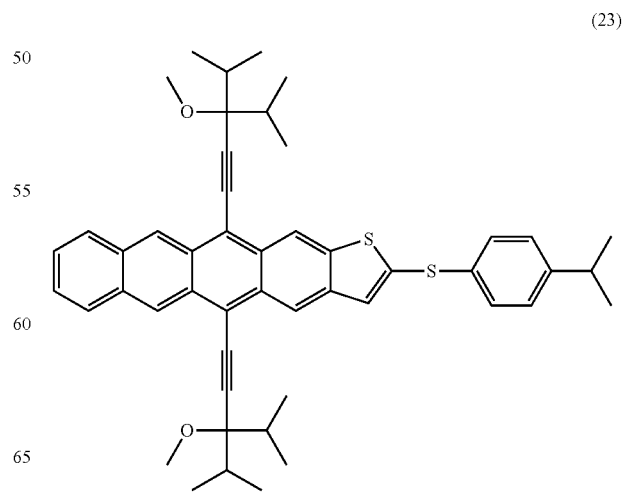
(23)

(24)
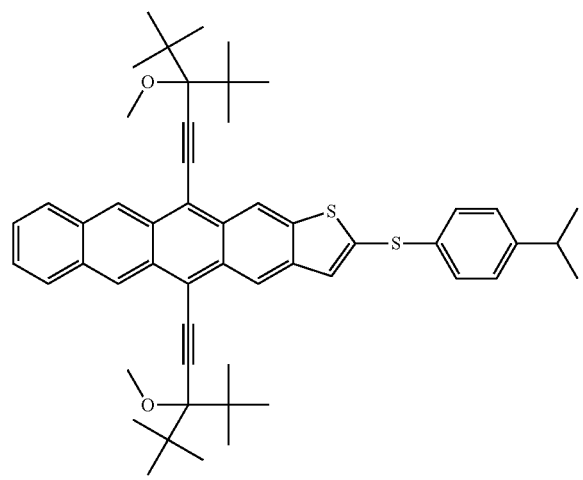
(25)
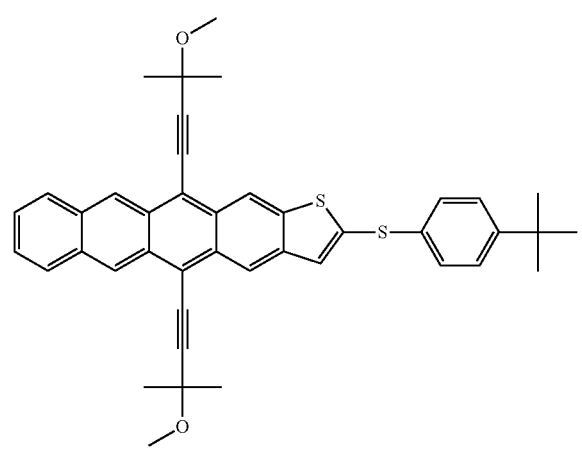
(26)
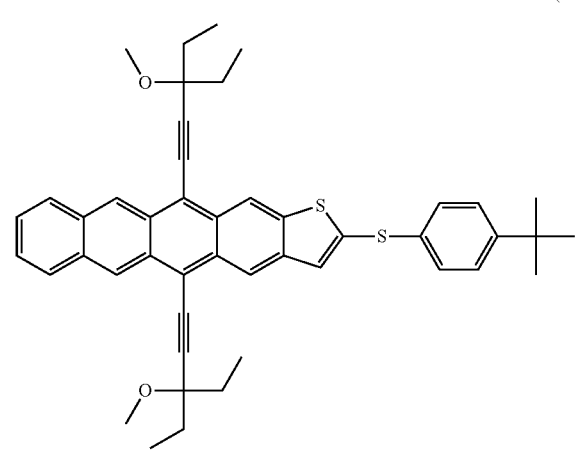
(27)
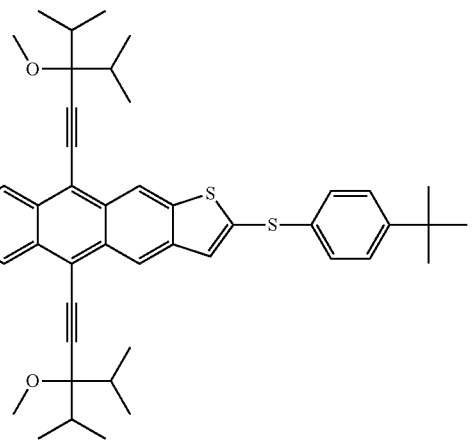
(28)
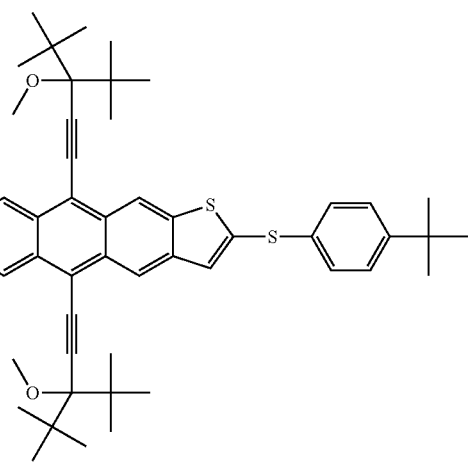
(29)
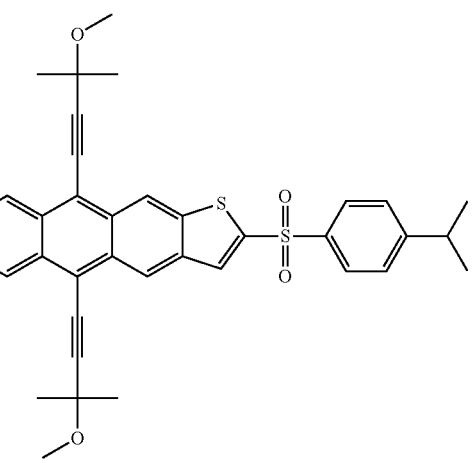

(30)
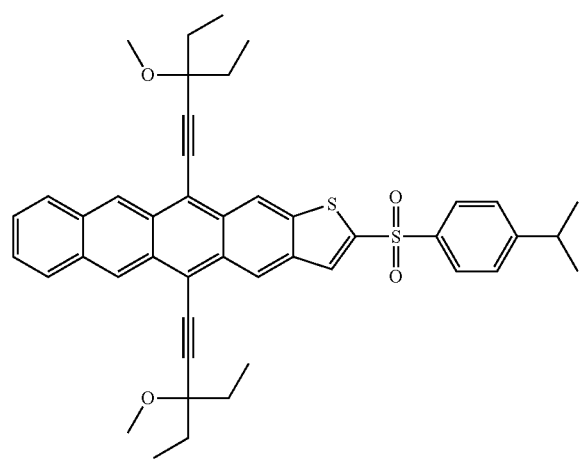
(33)
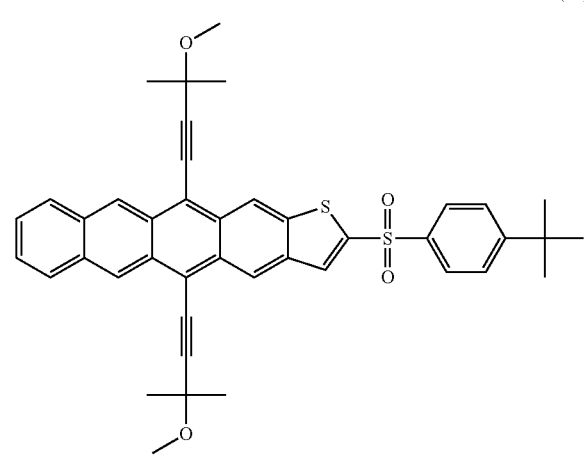
(31)
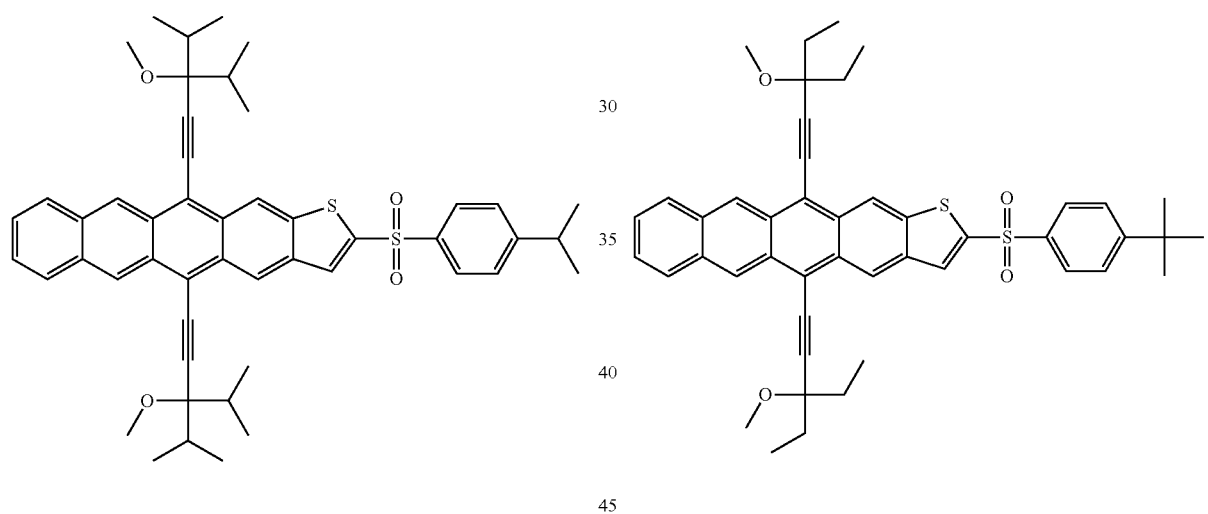
(32)
(34)
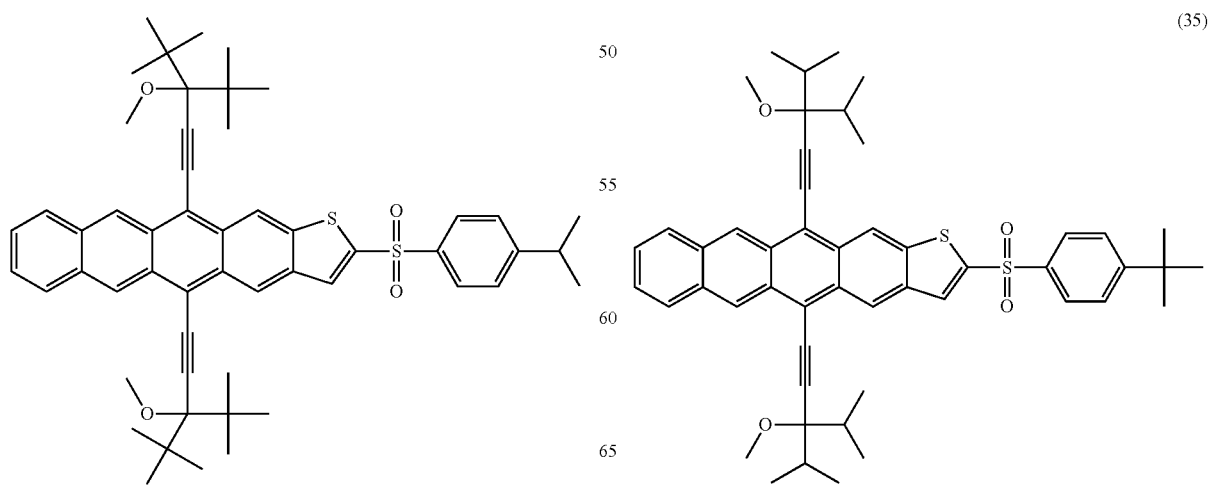
(35)

(36)
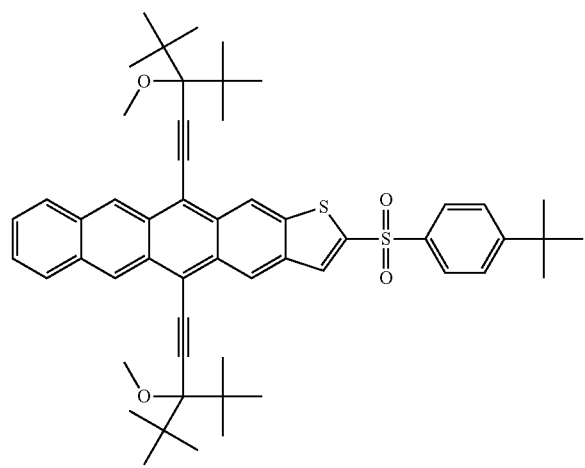
(37)
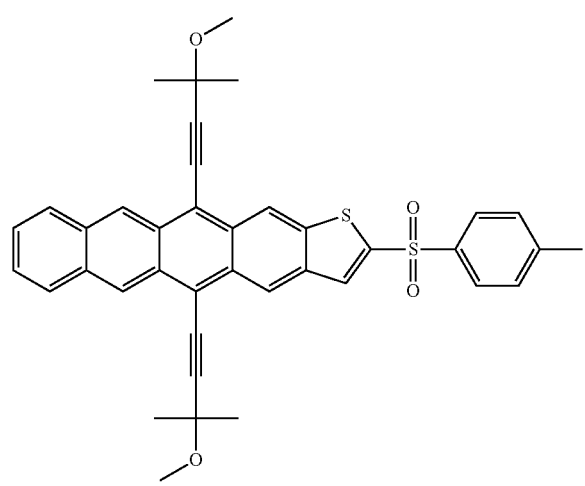
(38)
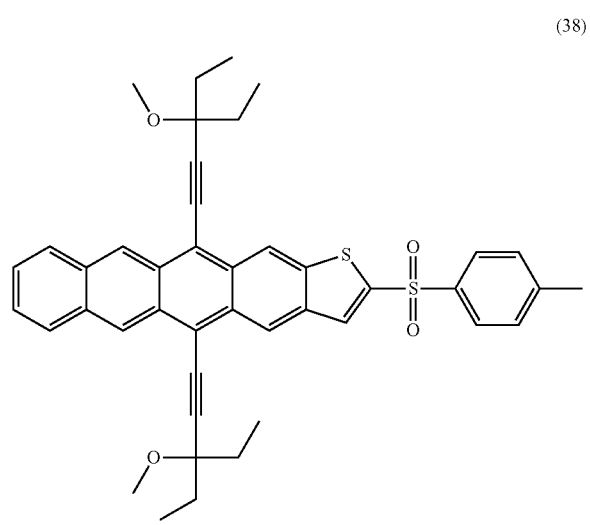
(39)
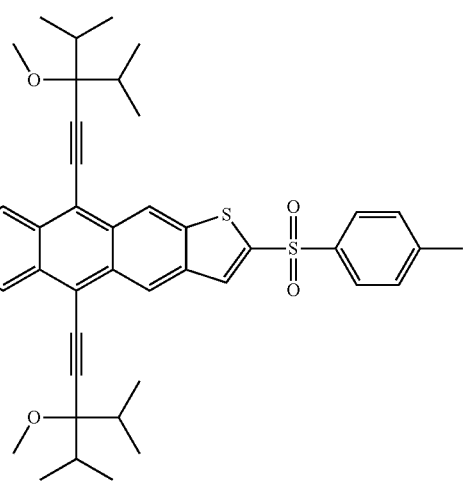
(40)
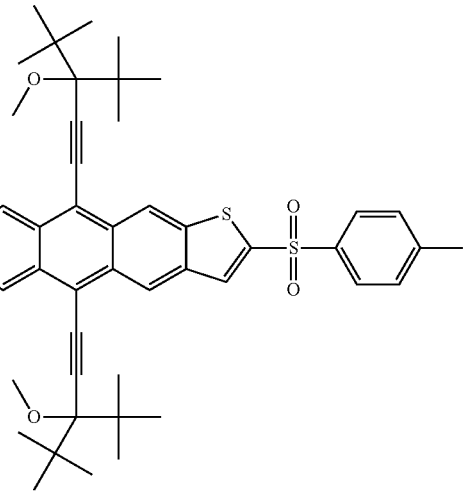
(41)
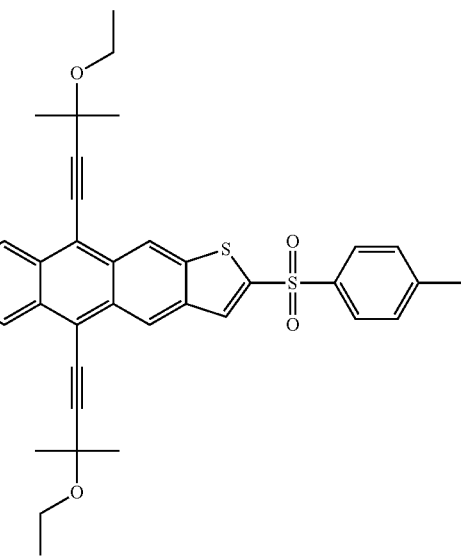

-continued
(42)
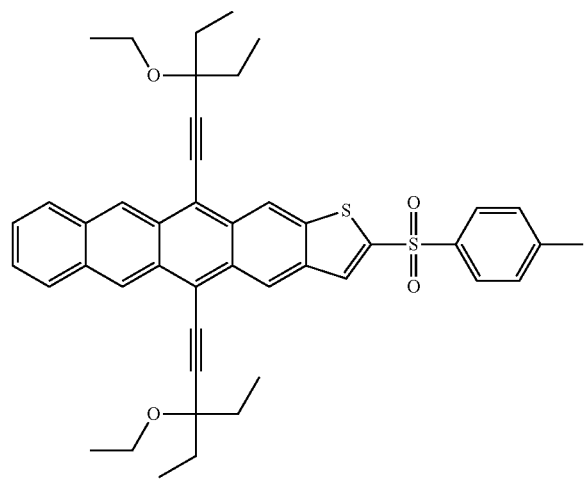
(45)
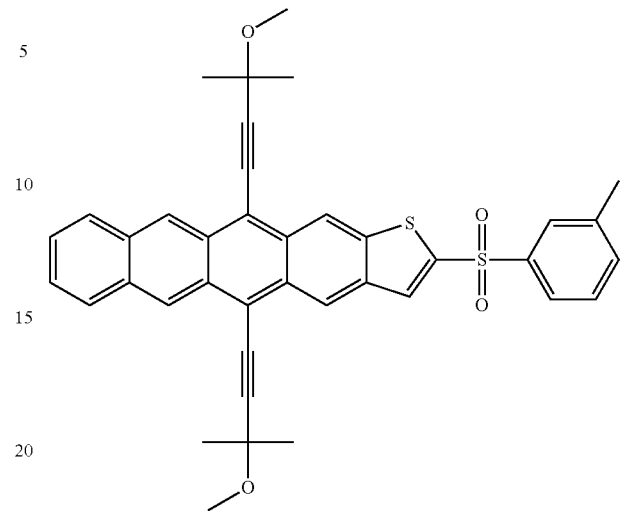
(43)
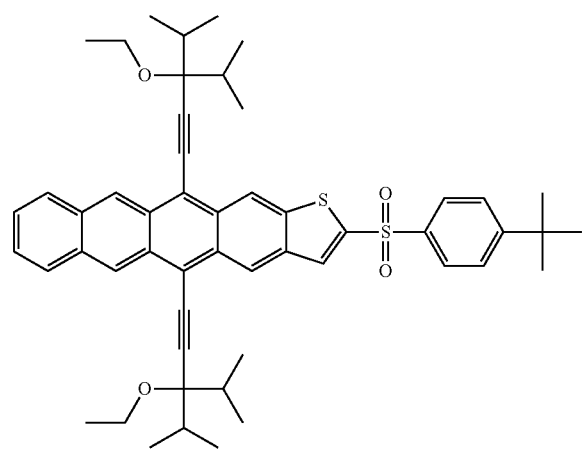
(46)
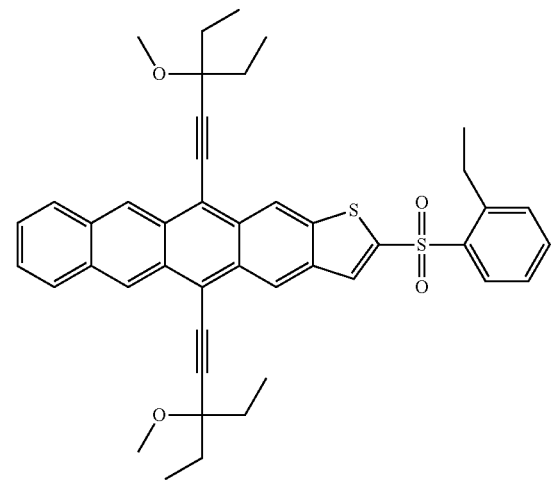
(44)
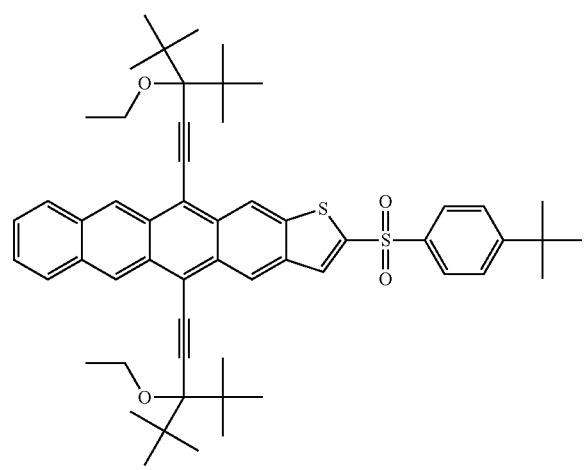
(47)
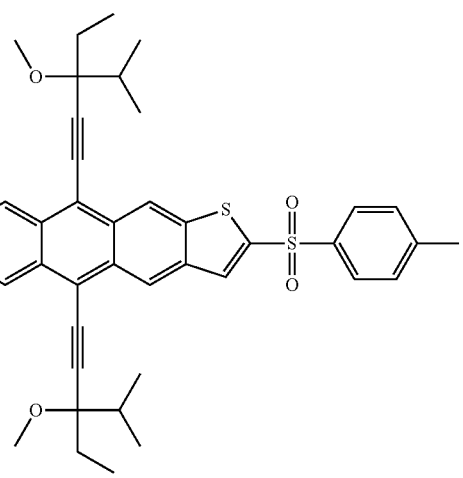

-continued
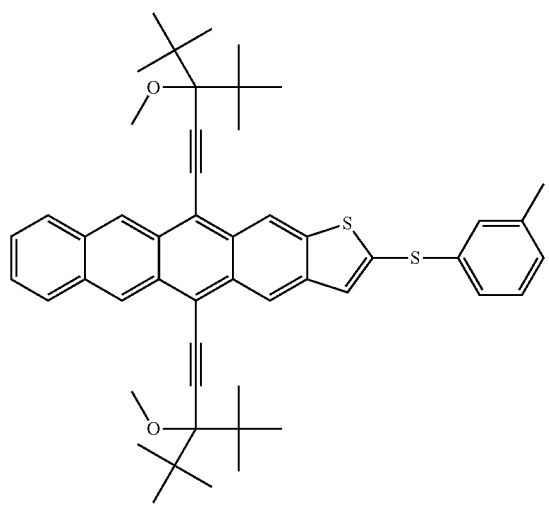
(48)
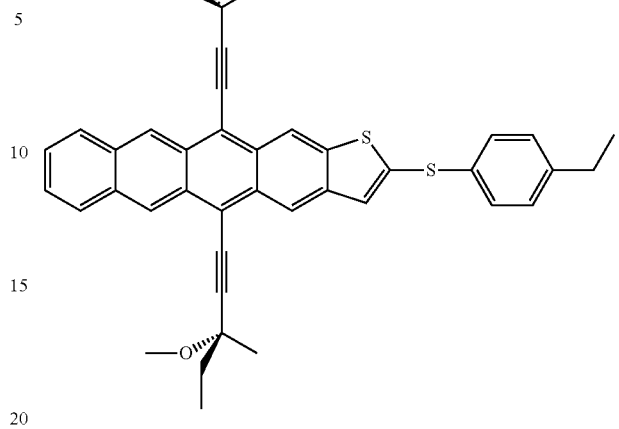
(51)
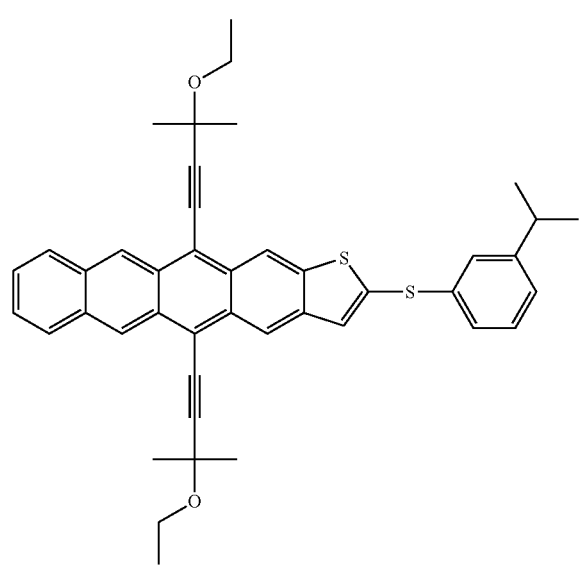
(49)
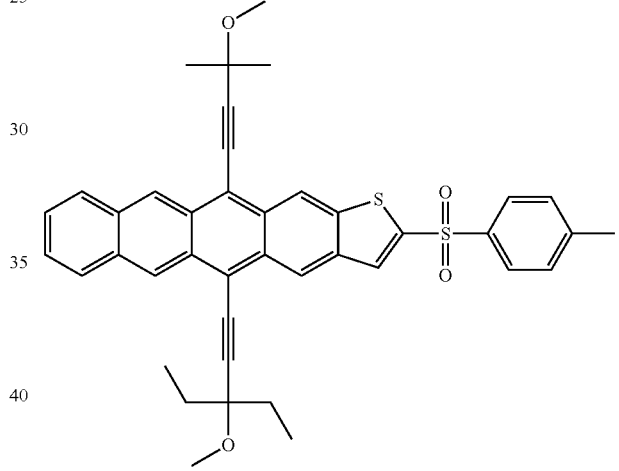
(52)
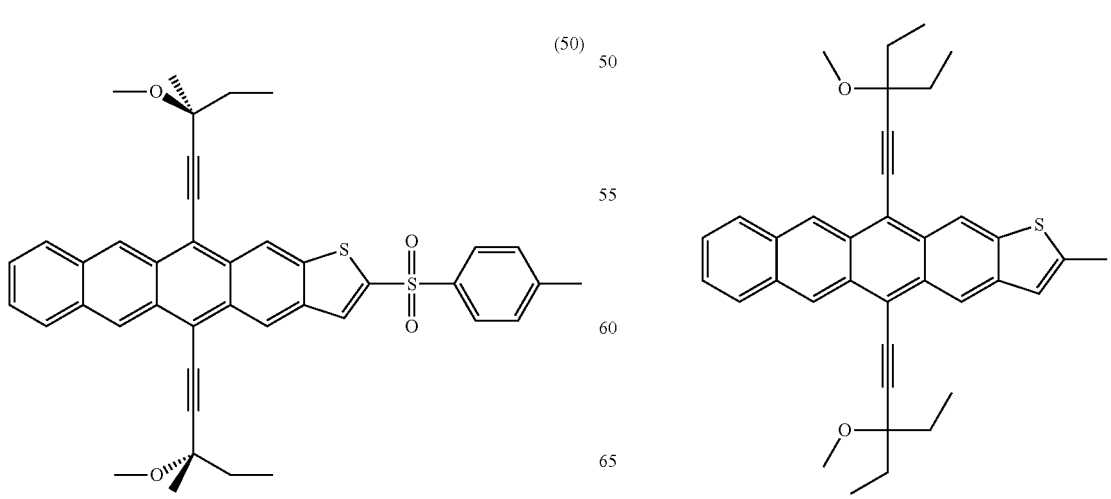
(50)
(53)

-continued
(54)
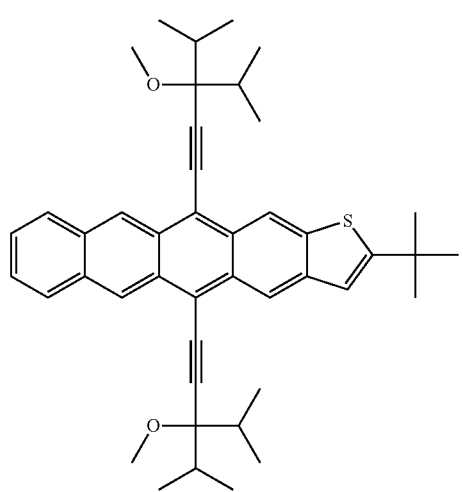
(57)
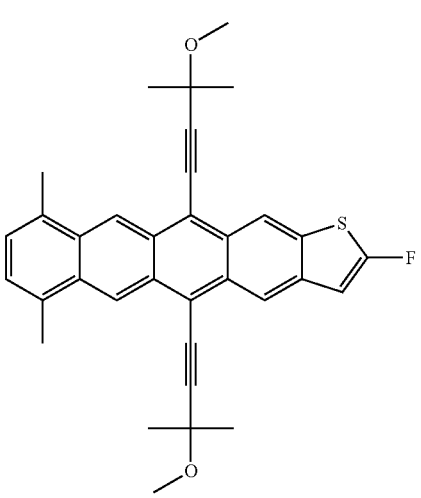
(55)
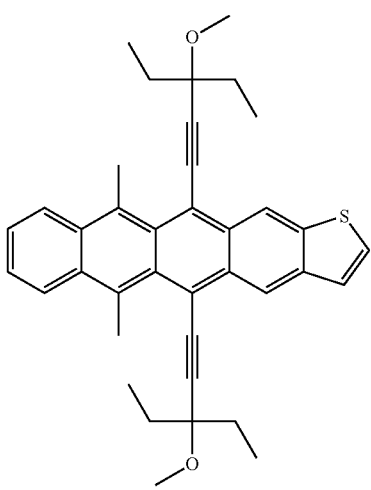
(58)
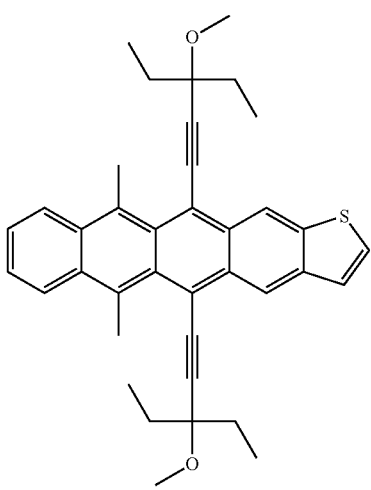
(56)
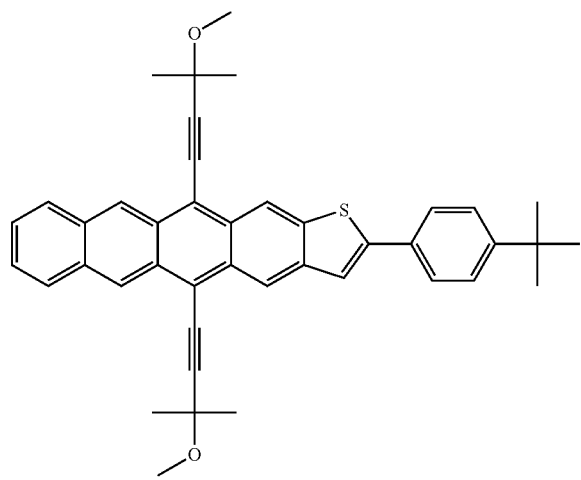
(59)
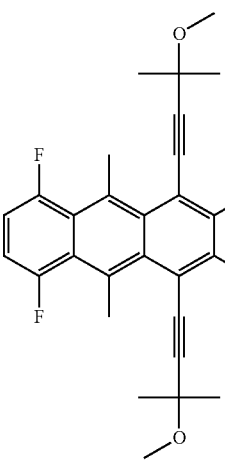

25
-continued
(60)
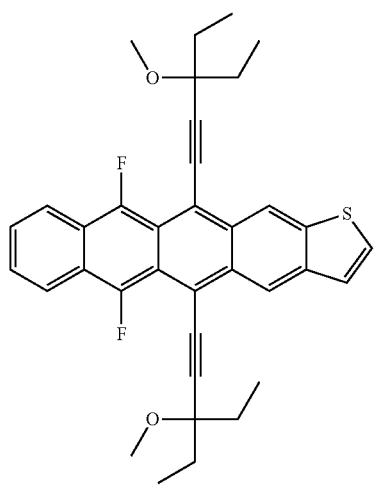
(61)
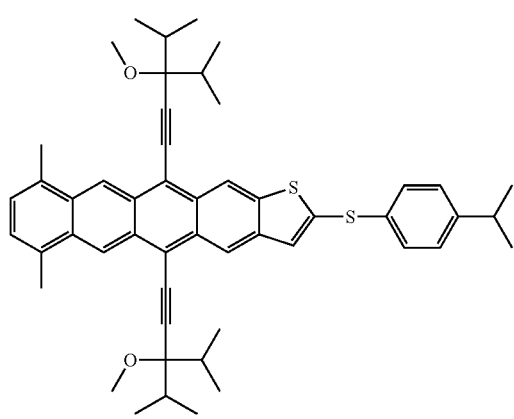
(62)
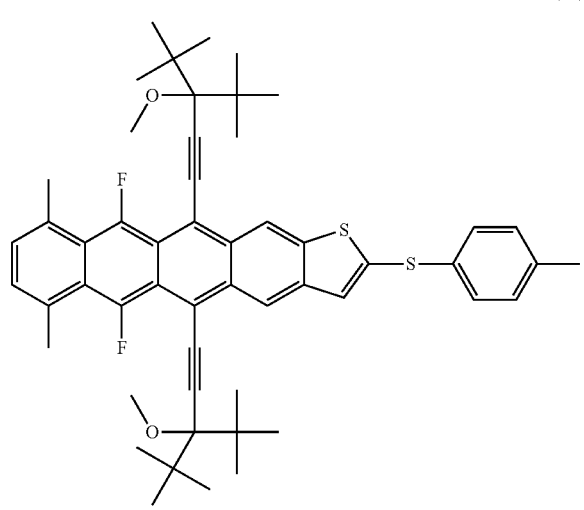
26
-continued
(63)
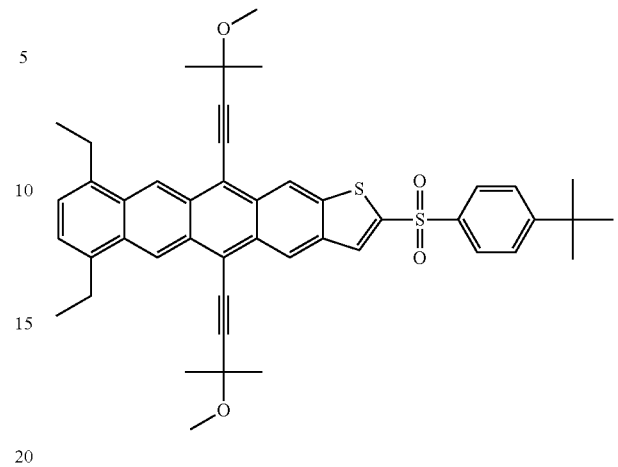
(64)
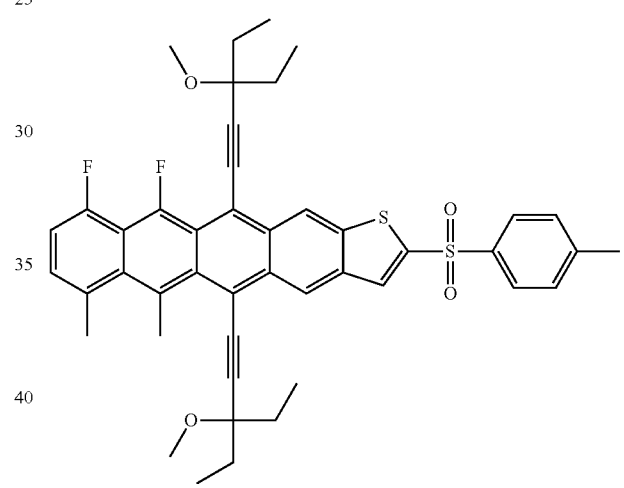
(65)
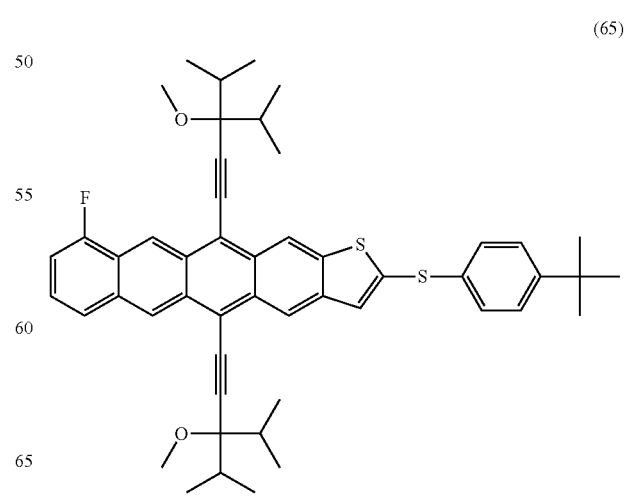

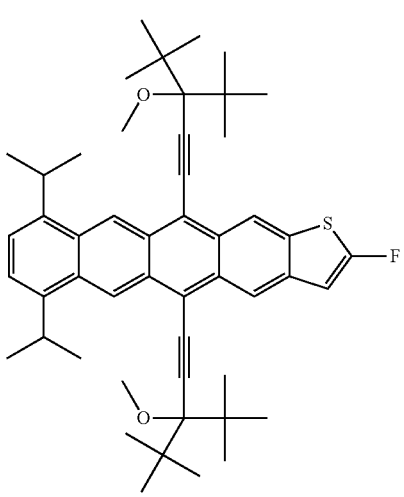
(66)
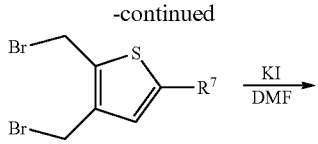
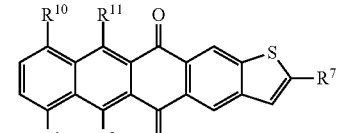
Synthesis of Tetracenothiophene Derivatives
The compounds of the present invention may be synthesized in analogy to methods known to the skilled artisan or according to the following general synthetic route:
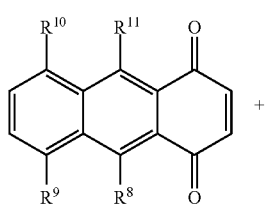
+
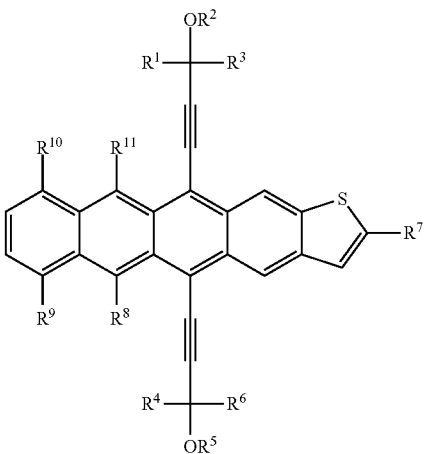
An exemplary method for the synthesis of compound (58) in present invention is shown in the following scheme:
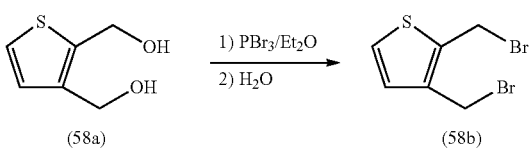
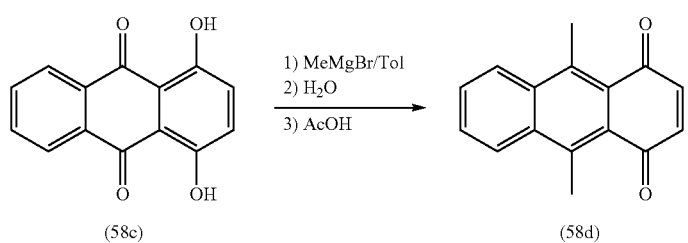

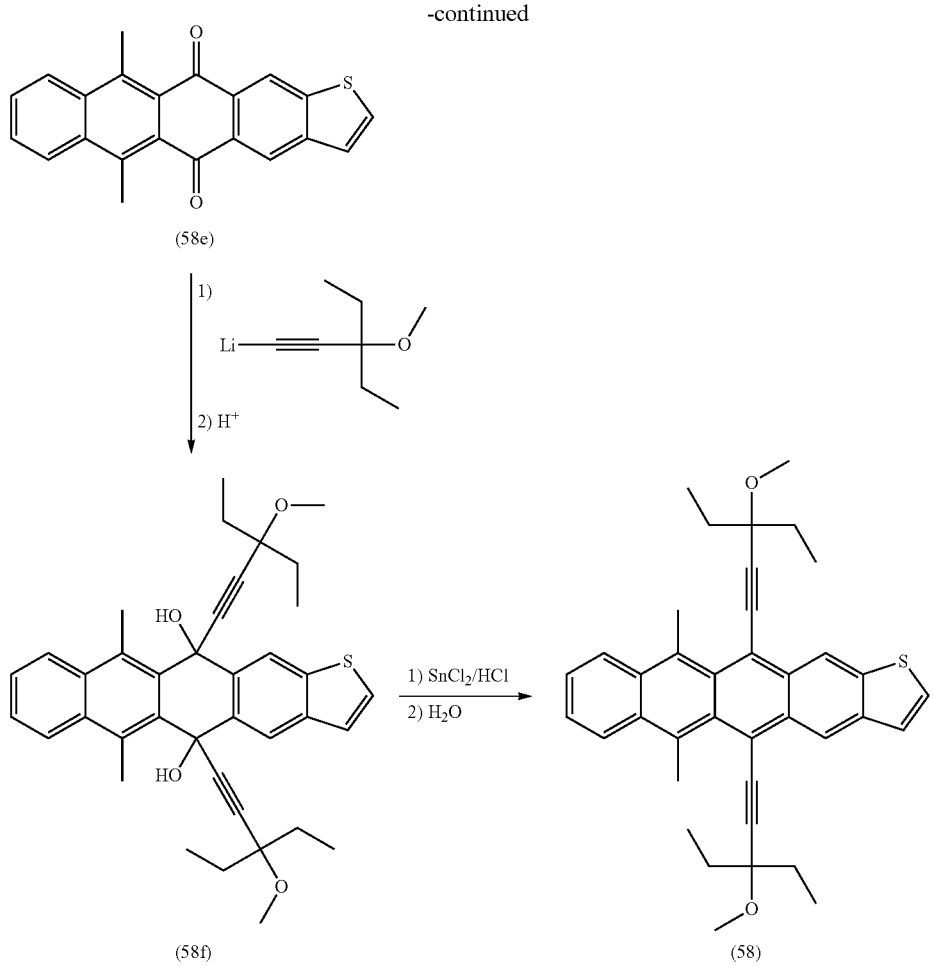

Intermediate (58d) can be prepared by treatment of 1,4-dihydroxyanthracene-9,10-dione (58c) with MeMgBr in Toluene/THF (3:1) at RT followed by reflux for 16 h. After quenching with water the separated organic layer was concentrated and treated with acetic acid under reflux for 4 h. The crude product can be purified by column chromatography using 5% EtOAc/Heptane as eluent. The diketone (58e) may be obtained by treatment of a suspension of (58b) and (58d) with KI in DMF at 80° C. for 20 h. The crude yellow powder of (58e) may be isolated by adding the reaction mixture into MeOH with stirring at 0° C. and purified by recrystallization from EtOAc/Hep. The dihydroxy intermediate (58f) may be made by treatment of diketone (58e) with excess (6 eq.) of lithiated alkyne followed by quenching with 10% aq. HCl. The crude product may be purified by neutral alumina column chromatography using 10% dichloromethane/heptane followed by recrystallization from EtOAc/heptane giving white powder (>99.5% HPLC). The OSC material (58) can be prepared from intermediate (58f) by treatment with $SnCl_2$/3M HCl in anhydrous THF at RT while protecting the flask from light. Highly pure (>99.6% HPLC) of compound (58) may be obtained by column chromatography purification followed by repeated precipitation from $CH_2Cl_2$/MeOH.

Organic Semiconductor Thin Films and their Applications

In a further embodiment, the present invention relates to organic thin films comprising the above-described tetracenothiophene compounds.

For the preparation of such organic thin films, the compounds according to the present invention may be used on their own or in combination with a polymer to form an organic material blend.

The organic thin films may be fabricated by depositing the tetracenothiophene derivatives according to the first embodiment of the present invention on a substrate according to conventional methods known in the art, or alternatively dissolving said compounds in an organic solvent (optionally together with the polymer) and then coating the same at room temperature according to a solution process. After the deposition or coating process, a heating treatment may be performed to further enhance the densification and uniformity of the thin film. The method of film deposition may include thermal deposition, vacuum deposition, laser deposition, screen printing, printing, imprinting, spin casting, dipping, inkjetting, roll coating, flow coating, drop casting, spray coating, and/or roll printing, for example. Preferred solution deposition techniques include spin coating and ink jet printing.

The organic solvent is not particularly limited and may include an aliphatic hydrocarbon (e.g. hexane or heptane), a haloalkane (e.g. chloroform), an aromatic hydrocarbon (e.g. toluene, pyridine, tetralin, quinoline, anisole, mesitylene, or xylene), a ketone (e.g. methyl isobutyl ketone, 1-methyl-2-pyrrolidinone, cyclohexanone, or acetone), an ether (e.g. tetrahydrofuran or isopropyl ether), an acetate (e.g. ethyl acetate, butyl acetate, or propylene glycol methyl ether acetate), an alcohol (e.g. isopropyl alcohol or butanol), an amide (e.g. dimethyl acetamide or dimethyl formamide), a silicone, and a mixture thereof. The type and amount of the solvent relative to the tetracenothiophene derivative may be appropriately selected and determined by a person of ordinary skill in the art.

The thickness of the organic thin films is not particularly limited and may be adjusted appropriately by the skilled artisan depending on their application. Usually, thicknesses of 1 µm or less are used, and for use in OFETs or OLEDs, the layer thickness is preferably 500 nm or less.

If the compounds according to the present invention are used in combination with a polymer to form an organic material blend, the polymer may be a polymeric binder in accordance with those disclosed in WO 2012/076092 A1, for example.

The organic thin films according to the present invention may be used as charge transport, semiconducting, electrically conducting, photoconducting or light emitting material in electronic devices and components.

Examples of electronic devices including the organic thin film as a carrier transport layer may include a transistor, an organic light emitting diode (OLED), a photovoltaic device, a solar cell, a laser device, a memory, and/or a sensor, and the organic thin film may be applied to each device according to a conventional process commonly known in the art.

In a preferred embodiment, the organic thin films according to the present invention may are used as semiconducting layers in electronic components, such as organic thin film transistors (OTFT).

An exemplary configuration of an OTFT is shown in FIG. 1, illustrating the general architecture of a bottom-gate OTFT. Herein, a gate electrode 12 is deposited on a substrate 10. An insulating layer 11 of dielectric material is deposited over the gate electrode 12 and source and drain electrodes 13, 14 are deposited over the insulating layer 11 of dielectric material. The source and drain electrodes 13, 14 are spaced apart to define a channel region therebetween located over the gate electrode 12. The organic semiconductor material 15 is deposited in the channel region for connecting the source and drain electrodes 13, 14. The organic semiconductor material 15 may extend at least partially over the source and drain electrodes 13, 14.

As an alternative to the bottom-gate OTFT, the gate electrode may be provided at the top of an organic thin film transistor to form a so-called top-gate OTFT. In such an architecture, source and drain electrodes are deposited on a substrate and spaced apart to define a channel region therebetween. A layer of an organic semiconductor material is deposited in the channel region to connect the source and drain electrodes and may extend at least partially over the source and drain electrodes. An insulating layer of dielectric material is deposited over the organic semiconductor material and may also extend at least partially over the source and drain electrodes. A gate electrode is deposited over the insulating layer and located over the channel region.

In general, organic thin film transistors may be fabricated on rigid or flexible substrates. Rigid substrates may be selected from glass or silicon and flexible substrates may comprise thin glass or plastics such as poly(ethylene-terephthalate) (PET), poly(ethylene-naphthalate) (PEN), polycarbonate and polyimide, for example.

The gate electrode can be selected from a wide range of conducting materials for example a metal (e.g. gold) or metal compound (e.g. indium tin oxide). Alternatively, conductive polymers may be deposited as the gate electrode. Such conductive polymers may be deposited from solution using, for example, spin coating or ink jet printing techniques and other solution deposition techniques discussed above.

The insulating layer comprises a dielectric material selected from insulating materials having a high resistivity. The dielectric constant, k, of the dielectric material is typically around 2-3 although materials with a high value of k are desirable because the capacitance that is achievable for an OTFT is directly proportional to k, and the drain current ID is directly proportional to the capacitance. Thus, in order to achieve high drain currents with low operational voltages, OTFTs with thin dielectric layers in the channel region are preferred. The dielectric material may be organic or inorganic. Preferred inorganic materials include $SiO_2$, $SiN_x$ and spin-on-glass (SOG). Preferred organic materials are generally polymers and include insulating polymers such as poly vinylalcohol (PVA), polyvinylpyrrolidine (PVP), acrylates such as polymethylmethacrylate (PMMA) and benzocyclobutanes (BCBs), for example. The insulating layer may be formed from a blend of materials or comprise a multi-layered structure.

Figure 2:
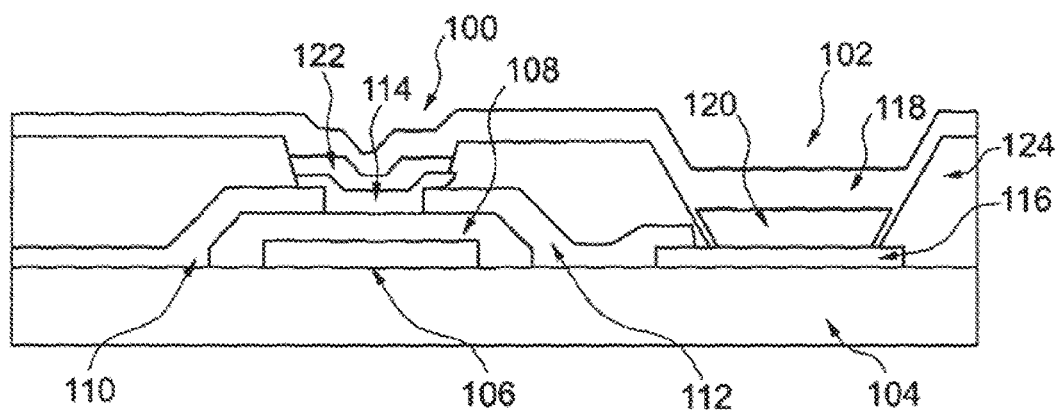
FIG. 2 schematically illustrates a pixel comprising an organic thin film transistor and an adjacent organic light-emitting device fabricated on a common substrate.

FIG. 2 shows a pixel comprising an organic thin film transistor 100 and an adjacent organic light-emitting device (OLED) 102 fabricated on a common substrate 104. The OTFT 100 comprises gate electrode 106, dielectric layer 108, source and drain electrodes 110 and 112 respectively, and OSC layer 114. The OLED 102 comprises anode 116, cathode 118 and an electroluminescent layer 120 provided between the anode 116 and cathode 118. Further layers may be located between the anode 116 and cathode 118, such as charge transporting, charge injecting or charge blocking layers. In the embodiment of FIG. 2, the layer of cathode material 118 extends across both the OTFT 100 and the OLED 102, and an insulating layer 122 is provided to electrically isolate the cathode layer 118 from the OSC layer 114. The active areas of the OTFT 100 and the OLED 102 are defined by a common bank material formed by depositing a layer of photoresist 124 on substrate 104 and patterning it to define OTFT 100 and OLED 102 areas on the substrate.

In FIG. 2, the drain electrode 112 is directly connected to the anode 116 of the organic light-emitting device 102 for switching the organic light-emitting device 102 between emitting and non-emitting states.

Figure 3:
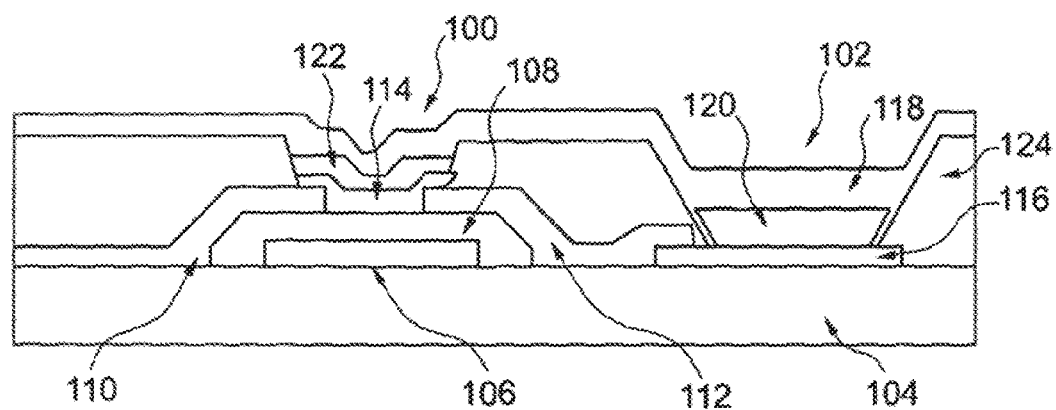
FIG. 3 schematically illustrates a stacked configuration comprising an organic thin film transistor and an organic light-emitting device.
Figure 4:
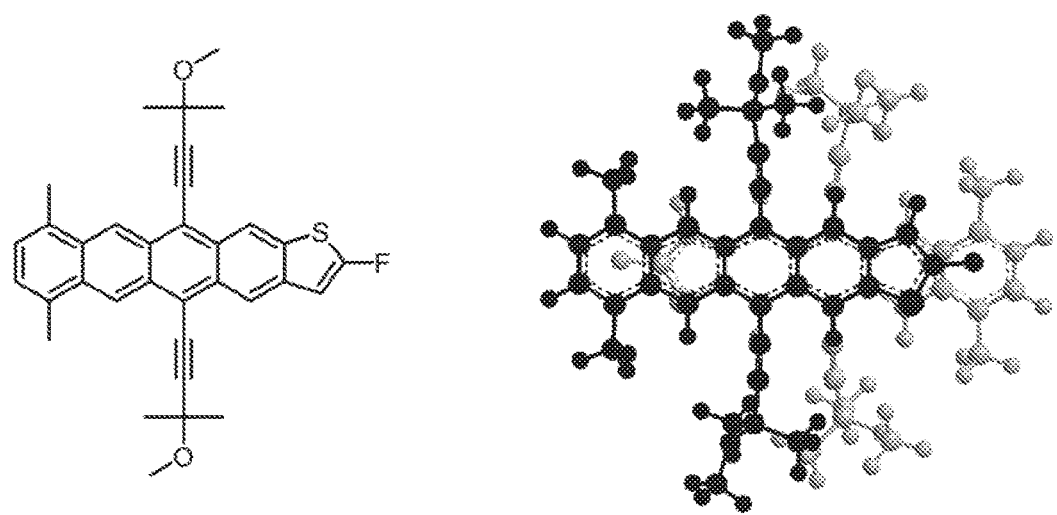
FIG. 4 shows calculated stacking structure of a compound of the present invention (optimized by LC-wPBE/6-31G*).

In an alternative arrangement illustrated in FIG. 3, an organic thin film transistor 200 may be fabricated in a stacked relationship to an organic light-emitting device 202. In such an embodiment, the organic thin film transistor 202 is built up as described above in either a top or bottom gate configuration. As with the embodiment of FIG. 2, the active areas of the OTFT 200 and OLED 202 are defined by a patterned layer of photoresist 124, however in this stacked arrangement, there are two separate bank layers 124—one for the OLED 202 and one for the OTFT 200. A planarisation layer 204 (also known as a passivation layer) is deposited over the OTFT 200. Exemplary passivation layers 204 include BCBs and parylenes. The organic light-emitting device 202 is fabricated over the passivation layer 204 and the anode 116 of the organic light-emitting device 202 is electrically connected to the drain electrode 112 of the OTFT 200 by a conductive via 206 passing through passivation layer 204 and bank layer 124.

It will be appreciated that pixel circuits comprising an OTFT and an optically active area (e.g. light emitting or light sensing area) may comprise further elements. In particular, the OLED pixel circuits of FIGS. 2 and 3 will typically comprise least one further transistor in addition to the driving transistor shown, and at least one capacitor. It will be appreciated that the organic light-emitting devices described herein may be top or bottom-emitting devices. That is, the devices may emit light through either the anode or cathode side of the device. In a transparent device, both the anode and cathode are transparent. It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium.

Transparent cathodes are particularly advantageous for active matrix devices because emission through a transparent anode in such devices may be at least partially blocked by OTFT drive circuitry located underneath the emissive pixels as can be seen from the embodiment illustrated in FIG. 3.

Other layers may be included in the device architecture. For example, in addition to providing a self assembled monolayer (SAM) on the gate, source or drain electrodes one may be provided on the, substrate, insulating layer and organic semiconductor material to promote crystallinity, reduce contact resistance, repair surface characteristics and promote adhesion where required. In particular, the dielectric surface in the channel region may be provided with a monolayer comprising a binding region and an organic region to improve device performance, e.g. by improving the organic semiconductor's morphology (in particular polymer alignment and crystallinity) and covering charge traps, in particular for a high k dielectric surface. Exemplary materials for such a monolayer include chloro- or alkoxy-silanes with long alkyl chains, e.g. octadecyltrichlorosilane.

Once given the above disclosure, many other features, modifications, and improvements will become apparent to the skilled artisan.

EXAMPLES

Reorganization Energies and Hole Mobility

Quantum chemical calculations were performed with the hybrid density functional theory (DFT) method using B3LYP and the 6-31G* (5d) basis set according to methods known in the art in order to determine the reorganization energies of tetracenothiophene derivatives according to the present invention. Reorganization energy ($\lambda$) is an important molecular factor that may affect charge transport properties of OSC materials. Carrier transport in organic solids is often described by the hopping model, where the high mobility, i.e. rapid exchange of carriers between molecules can be realized by a small energy, $\lambda$(energy consumption during carrier exchange at the molecular level). For p-type OSC materials largely $\gamma$-extended compounds tend to have smaller $\lambda^h$ ($\lambda$ for hole) values in general, because of the effective delocalization of hole in the radical cation state, which reduces structural deformation during carrier transport. A smaller $\lambda^h$ value stands for better transport properties.

In particular, the reorganization energies of compounds (1), (5), and (57) have been calculated in accordance with procedures described in the literature (see e.g. J. Phys. Chem. A, 2003, 107, 5241-5251).

Figure 5:
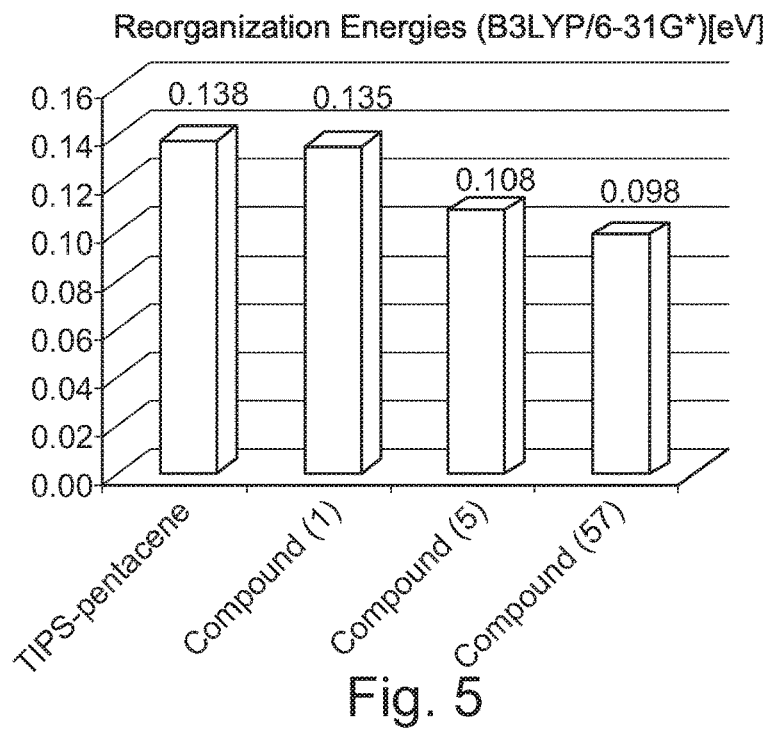
FIG. 5 shows the reorganization energies of compounds of the present invention comparison with that of TIPS-pentacene.
Figure 6:
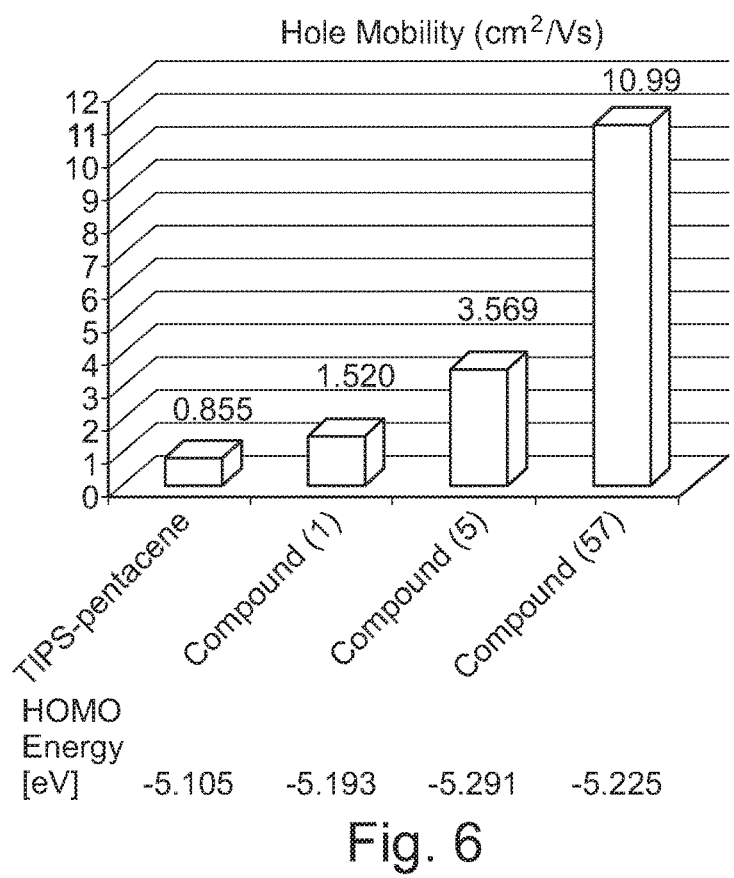
FIG. 6 shows predicted hole mobiles (B3LYP/6-31G*) of compounds of present invention comparison with that of TIPS-pentacene

The results of the calculations are shown in FIG. 5 and FIG. 6. All values are quoted in electronvolts (eV).

As is demonstrated by the calculations, the tetracenothioacene derivatives according to the present invention exhibit smaller reorganization energies and improved hole mobilities when compared with TIPS-pentacene. Taking further into account that they at the same time exhibit sufficient solubility in typical organic solvents so they may be applied by a large variety of solution deposition techniques, it may be concluded that tetracenothioacene derivatives of the present invention represent excellent candidates for organic semiconductor applications.

Once given the above disclosure, many other features, modifications, and improvements will become apparent to the skilled artisan.

The invention claimed is:
1. A tetracenothioacene derivative represented by the following General Formula (I):

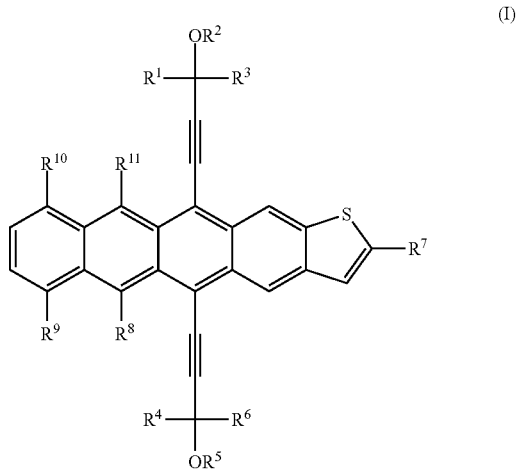

wherein $R^1$ to $R^6$ independently represent a $C_{1-12}$ alkyl group;
wherein $R^8$ to $R^{11}$ independently represent any one of a hydrogen atom, a halogen atom, or a $C_{1-6}$ alkyl group; and
wherein $R^7$ represents any one of a hydrogen atom, a halogen atom, a $C_{1-12}$ alkyl group or a substituent according to the following General Formula (II):

with X being a single bond, —S— or —SO$_2$—; and Z being a $C_{1-12}$ alkyl group.

2. The tetracenothioacene derivative according to claim 1, wherein the substituent Z is in para-position relative to the substituent X.

3. The tetracenothioacene derivative according to claim 1, wherein $R^1$, $R^3$, $R^4$ and $R^6$ are independently selected from any of a methyl, ethyl, isopropyl or tert-butyl group, and/or wherein $R^8$ to $R^{11}$ are independently selected from any of a hydrogen atom, a fluorine atom, or an methyl group.

4. The tetracenothioacene derivative according to claim 1, wherein $R^2$ and $R^5$ are identical and preferably represent methyl groups.

5. The tetracenothioacene derivative according to claim 1, wherein Z is selected from any of a methyl, ethyl, isopropyl or tert-butyl group.

6. The tetracenothioacene derivative according to claim 1, wherein $R^1$ and $R^3$ are identical and/or $R^4$ and $R^6$ are identical.

7. The tetracenothioacene derivative according to claim 1, wherein $R^1$, $R^3$, $R^4$ and $R^6$ are identical.

8. The tetracenothioacene derivative according to claim 1, wherein the halogen atom is a fluorine atom.

9. The tetracenothioacene derivative according to claim 1, wherein the residues $R^1$, $R^3$, $R^4$ and $R^6$ are different from Z.

10. The tetracenothioacene derivative according to claim 1, wherein the residues $R^1$, $R^3$, $R^4$, $R^6$ and Z are identical.

11. An organic thin film comprising a tetracenothioacene derivative according to claim 1.

12. The organic thin film according to claim 11, further comprising a polymer.

13. An electronic device or component comprising an organic thin film according claim 11.

14. A solution for applying to the surface of a substrate to form a semiconducting portion on the substrate, the solution comprising a tetracenothioacene derivative according to claim 1.

15. A method of manufacturing an electronic device or component, the method comprising applying a solution comprising a tetracenothioacene derivative according to claim 1 to a substrate.

* * * * *